DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED MARCH 7, 1972

896 O.G. 16

T896,001

HIGH PURITY POLYESTER DEPOLYMERIZATION PRODUCTS FROM POLYESTER SCRAP BY COMPLETE HYDROGENATION

George Miller Stevenson, Kingsport, Tenn., assignor to Eastman Kodak Company, Rochester, N.Y.

Continuation of application Ser. No. 676,724, Oct. 20, 1967. This application Nov. 24. 1969, Ser. No. 873,728

Int. Cl. C07c *35/02;* C08g *17/08*

U.S. Cl. 260—617C

No Drawing. 15 Pages Specification

A substantially colorless cyclohexanedimethanol solution is produced by depolymerizing scrap polyesters of difunctional glycols and difunctional aromatic dicarboxylic acids in the presence of a $C_2$ to $C_8$ aliphatic alcohol at a temperature of at least about 125° C. so as to obtain a depolymerized reaction product comprising a diester, subjecting the diester to a first catalytic hydrogenation reaction under conditions sufficient to saturate the aromatic ring of the diester, and then subjecting the resulting diester to a second catalytic hydrogenation reaction under conditions sufficient to reduce the ester groups and to produce the substantially colorless cyclohexanedimethanol.